United States Patent [19]

Cole et al.

[11] 4,291,702
[45] Sep. 29, 1981

[54] CATHETER FLUSHING APPARATUS

[75] Inventors: James E. Cole; Peter Thornton, both of Ventura, Calif.

[73] Assignee: Gould Inc., Rolling Meadows, Ill.

[21] Appl. No.: 52,019

[22] Filed: Jun. 25, 1979

[51] Int. Cl.³ .............................................. A61B 5/02
[52] U.S. Cl. ................................ 128/675; 128/214 E; 137/238; 251/117
[58] Field of Search ........... 128/214 E, 214 F, 214 R, 128/675, 274, DIG. 13, DIG. 12, 672-674; 251/117; 137/238

[56] References Cited

U.S. PATENT DOCUMENTS

| 1,005,409 | 10/1911 | Bruns | 251/117 X |
| 2,411,667 | 11/1946 | Mowrey | 251/117 X |
| 2,655,170 | 10/1953 | Ferguson | 251/117 X |
| 2,955,614 | 10/1960 | Meynig | 251/117 X |
| 3,298,367 | 1/1967 | Bergman | 128/214 R |
| 3,474,816 | 10/1969 | Burgess | 137/238 |
| 3,675,891 | 7/1972 | Reynolds et al. | 251/117 |
| 3,877,428 | 4/1975 | Seagle et al. | 128/214 R |

Primary Examiner—Kyle L. Howell

[57] ABSTRACT

A flow control apparatus is disclosed which is particularly useful in liquid flow systems for blood pressure monitoring in humans and other animals. A resiliently biased valve plunger is provided with a marine bore capillary passage extending from one side of the plunger seating area to the other, thus establishing a first, low flow path. When the plunger is moved from its seat, a second, high flow path is established which flushes the apparatus. In one embodiment, the apparatus is combined with a pressure transmitting diaphragm assembly used to transmit pressure to instrumentation, the flush flow then serving to sweep air from the plenum above the diaphragm.

8 Claims, 2 Drawing Figures

CATHETER FLUSHING APPARATUS

BACKGROUND OF THE INVENTION

The present invention relates to flow control apparatus for use in fluid flow catheters of the type found in blood pressure and dynamics measurement systems. In such systems, a catheter commonly is inserted into a patient's vein to a location where measurements are desired. The catheter is maintained full of a neutral, sterile solution, which actually flows into the patient at a very low rate of, say, 3 ml/hr. This low flow is required to keep the catheter open, or patent, throughout its length, by preventing the ingress of blood constituents at the in-dwelling end of the catheter. By monitoring changes in the liquid pressure in the catheter, a variety of useful data can be obtained regarding the blood pressure, flow, etc. at the in-dwelling end.

When such catheters are prepared for use, they must be flushed completely of all air which could be harmful to the patient. Since the normal small flow rate would cause the device to fill very slowly, provisions have been made in the prior art for providing a second, much higher flow rate (perhaps 30 ml/min.) for use during initial flush and fill of the catheter and during use to momentarily allow a higher flow rate into the patient to clear out any debris which may have collected at the in-dwelling end of the catheter. U.S. Pat. No. 3,675,891, issued July 12, 1972 to Gordon S. Reynolds and others, discloses one prior art catheter flushing apparatus. The present invention embodies improvements upon the Reynolds device.

OBJECTS OF THE INVENTION

A primary object of this invention is to provide an improved catheter flushing apparatus which is simpler in construction than prior art devices, without loss of reliability.

Another object of the invention is to provide such an apparatus in combination with a pressure transmitting diaphragm assembly, in such a manner that the diaphragm assembly is adequately flushed of air at the same time as the catheter.

Still another object of the invention is to provide such a device which is configured for ease of manufacture using conventional injection molding techniques.

A further object of the invention is to provide such an apparatus with provision for overpressure release, to prevent damage to associated pressure instrumentation.

Still another object of the invention is to provide such an apparatus which is suited for single hand actuation, thus simplifying its use.

Another object of the invention is to provide such an apparatus which is inexpensive and economically disposable following use.

These objects are given only by way of example; thus, other desirable objectives and advantages inherently achieved by the disclosed invention may occur to those skilled in the art. Nonetheless, the scope of the invention is to be limited only by the appended claims.

SUMMARY OF THE INVENTION

The above objects and other advantages are achieved by the invention, in which a flow passage having an inlet and outlet is provided in a housing. A valve plunger slidably located within the housing is resiliently biased against a seat provided in the passage walls. The plunger includes a capillary passage which effectively bypasses the valve seat, thus permitting a first, low flow. When the plunger is moved from its seat, a second, high flow is established for flushing the device and its associated catheter. In one embodiment, the downstream end of the flow passage opens into a plenum bounded on its lower end by a flexible pressure transmitting diaphragm. The plenum is oriented and configured relative to the flow passage so that air in the plenum is easily flushed out during fill prior to use.

DETAILED DESCRIPTION OF THE PREFERRED EMBODIMENTS

Figure 1:
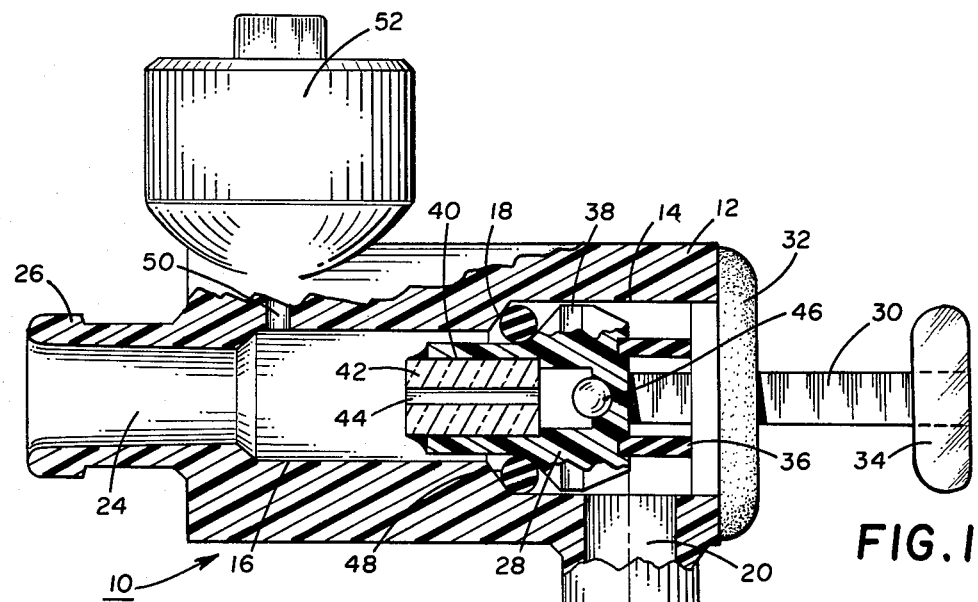
FIG. 1 shows an elevation view, partially in section, of one embodiment of the invention.

The following is a detailed description of the preferred embodiments of the invention, reference being made to the drawing in which like reference numerals identify like elements of structure in the Figures.

FIG. 1 shows an elevation view, partially in section, of one embodiment 10 of a flow control apparatus according to the invention. An essentially cylindrical housing 12 is provided with a first, larger interior bore 14 and a second, smaller interior bore 16, the two bores being joined by a conical valve seat 18 to provide a flow passage. An inlet passage 20 enters bore 14 from below, as illustrated, and is provided with a boss having a conventional attachment fitting 22. An outlet passage 24 leaves bore 16 essentially coaxially and is provided with a boss having a conventional attachment fitting 26. Housing 12 preferably is injection molded from a material such as clear polycarbonate plastic.

A valve plunger 28 is slidably mounted within bore 14. An actuator shaft 30 extends from the inlet end of valve plunger 28 through a hole provided in cap 32. An actuator knob or button 34 is provided on the outer end of shaft 30. A short, resilient spring cylinder 36 of a material such as silicone rubber is captured between and sealed to valve plunger 28 and cap 32. Spring cylinder 36 is sized so that when the apparatus is assembled as shown, valve plunger 28 is resiliently biased toward valve seat 18. Plunger 28 further includes a radially extending circumferential flange 38, which is sufficiently smaller in diameter than bore 14 to allow the desired liquid flow through the apparatus. The outlet end of valve plunger 28 is provided with a counterbore 40, in which a glass cylinder 42 is secured by suitable means. A capillary bore 44 is provided in cylinder 42, the bore diameter being chosen to provide the desired continuous flow rate through the apparatus in actual use and to damp out undesirable inlet pressure surges. At the bottom of counterbore 40, one or more radially extending passages 46 are provided which open into bore 14 on the inlet side of circumferential flange 38, to complete the continuous, low flow path through the apparatus. The outlet side of circumferential flange 38 is provided with a conical surface of geometry similar to that of valve seat 18. A resilient seal ring 48 of a material such as silicone rubber is captured between valve plunger 28 and seat 18. Ring 48 preferably is sized so that it moves with valve plunger 28 and is small enough in outer diameter to allow the desired maximum flush flow rate when valve plunger 28 is moved to the right, as illustrated. However, ring 48 also may be sized to fit snugly in bore 14 right at seat 18, in which case the inner diameter of the ring is sized to allow the desired maximum flush rate. Finally, an auxilliary outlet passage 50 is provided through a boss having an attachment fitting 52, to which suitable pressure instrumentation is attached during use.

In use, the apparatus is connected to receive liquid through inlet passage 20. The liquid flows into bore 14, through passages 46, through capillary bore 44 and out outlet passage 24. To speed flushing of air from the device prior to insertion of the catheter in a patient, actuator shaft 30 is moved to the right from the position shown in FIG. 1, thus permitting a much larger flow of liquid to shunt or bypass capillary bore 44 and thereby sweeping air from the apparatus. Once the catheter has been inserted into a patient, a slow continuous flush flow passes through capillary bore 44. Periodically, to ensure that the in-dwelling end of the catheter does not clog, actuator rod 30 is moved to allow a short, high flow burst of fluid to course through the system, thereby dislodging and sweeping away any undesirable particles. The spring constant of spring cylinder 36 is chosen so that should the pressure at the outlet end of the apparatus approach an undesirably high level for the pressure transducer operatively connected to auxilliary outlet passage 50, then valve plunger 28 will move to the right to equalize the pressures. Of course, the inlet pressure in passage 20 should not exceed the maximum allowable for the pressure instrumentation.

Figure 2:
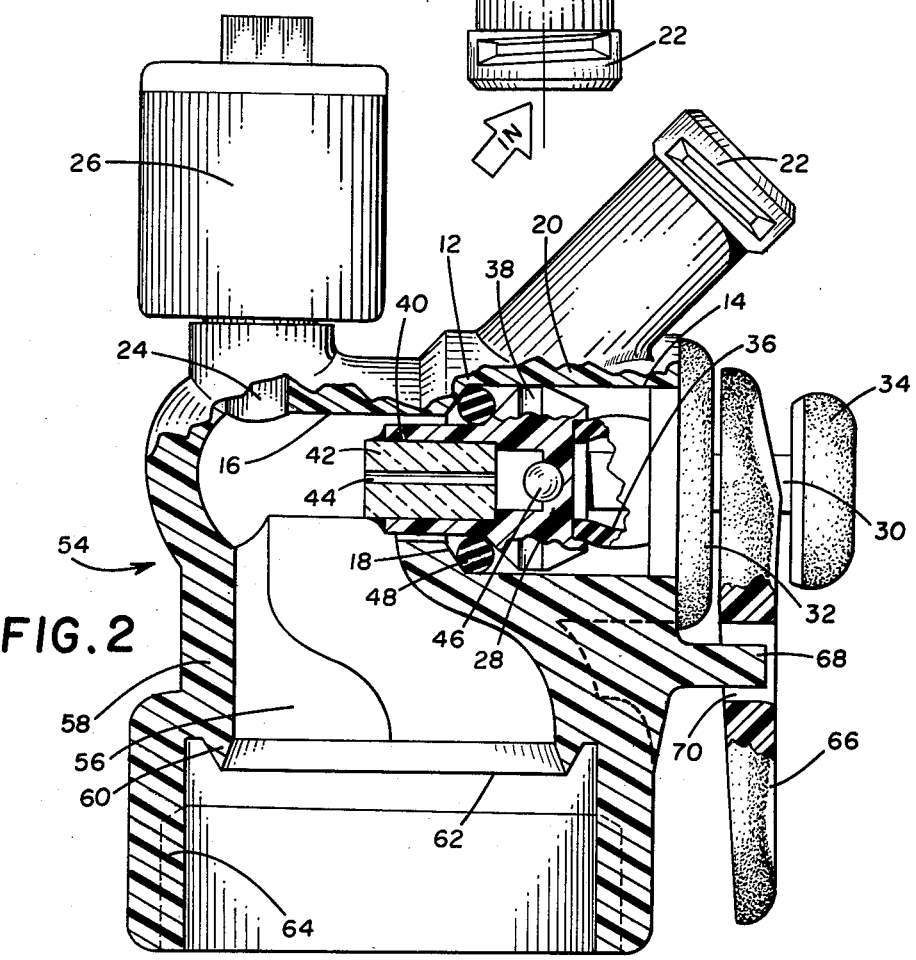
FIG. 2 shows an elevation view, partially in section, of another embodiment of the invention in which a pressure transmitting diaphragm is built into the apparatus.

FIG. 2 shows an elevation view, partially in section, of another embodiment 54 of a flow control device according to the invention. Here, outlet passage 16 opens downwardly, as illustrated, into a plenum 56 bounded by downwardly depending, generally outwardly flaring circumferential wall 58. The lower edge of wall 58 defines an annular lip 60 which is hermetically attached to a thin, flexible plastic diaphragm 62. Thus, liquid in plenum 56 causes diaphragm 62 to flex in response to pressure changes. These changes are transmitted to a liquid on the other side of diaphragm 62. The pressure in this other liquid is monitored by a transducer, not shown, attached to the apparatus by a suitable fitting 64. For simple actuation of the apparatus to provide high flush flow, a flush lever 66 is slidably mounted on actuator shaft 30. A retaining finger 68 extends from housing 12 into a bore 70 in lever 66, to keep the lever in position for convenient actuation.

In use, the apparatus of FIG. 2 operates virtually identically to that of FIG. 1. High flush flow is easily provided with one hand by gripping housing 12 and lever 66 between the thumb and forefinger and squeezing. Due to the downwardly flaring geometry of plenum 56 and the location of outlet passage 16 at the upper end thereof, air in plenum 56 is quickly and efficiently flushed from the device prior to insertion of the catheter in the patient. Also, since the flush flow and the low flow are directed essentially parallel to diaphragm 62, no unwanted distortion of the diaphragm results due to flow effects.

Having described our invention in sufficient detail to enable those skilled in the art to make and use it, we claim:

1. An improved flow control apparatus for use in liquid flow systems for pressure monitoring of hemodynamics, such systems including a catheter which is continuously flushed in use, said apparatus comprising:
 a housing having at least one passage therein, said passage having an inlet and an outlet;
 a valve seat defined in said passage;
 a valve plunger movably mounted in said passage;
 resilient means biasing said plunger into contact with said seat;
 capillary means extending at least partially through said plunger for providing a low flow path from said inlet to said outlet when said valve plunger is in contact with said valve seat;
 means for selectively moving said valve plunger out of contact with said valve seat to provide a high flow path around said plunger from said inlet to said outlet, said moving means including an actuator member attached to said plunger and slidably mounted in and extending through a hole extending from said passage to the exterior of said housing so that said plunger may be moved selectively out of contact with said seat by manipulation of said actuator member from externally of said housing; and
 a flexible sealing element connected about said actuator member and to said housing about said hole to prevent liquid from leaking out of said passage through said hole.

2. An improved flow control apparatus according to claim 1, wherein said housing comprises a plenum extending downwardly from said at least one passage, said plenum having a flexible lower diaphragm wall; and further comprising means located exteriorly of said diaphragm for attaching a pressure sensing device.

3. An improved flow control apparatus according to claim 2, wherein said plenum comprises downwardly extending, essentially smoothly flaring side walls, whereby gas trapped in said plenum is caused to rise as said plenum fills with liquid, to be flushed from the apparatus through said oulet.

4. An improved flow control apparatus according to claim 1, wherein said valve plunger comprises an essentially cylindrical body with an essentially radially extending circumferential flange thereon, a counterbore extending axially through said cylindrical body, said capillary means being mounted in said counterbore, and at least one passsage extending from said counterbore outward to an exterior surface of said cylindrical body.

5. An improved flow control apparatus according to claim 4, further comprising a resilient seal element positioned between said circumferential flange and said valve seat.

6. An improved flow control apparatus according to claim 5, wherein said seal element is a resilient ring having an outer diameter sized to permit flow of liquid through said passage when said valve plunger has been moved out of contact with said valve seat.

7. An improved flow control apparatus according to claim 5, wherein said seal element is a resilient ring having an inner diameter sized to permit flow of liquid through said passage when said valve plunger has been moved out of contact with said valve seat.

8. An improved flow control apparatus according to claim 1, wherein said moving means further includes a contact button mounted on the end of said actuator member extending to the exterior of said housing and lever means movably mounted on said housing in position to cooperate with said button to move said valve plunger out of contact with said valve seat.

* * * * *